US010892051B2

(12) United States Patent
Philippe et al.

(10) Patent No.: US 10,892,051 B2
(45) Date of Patent: Jan. 12, 2021

(54) SYSTEMS AND METHODS FOR AUTOMATICALLY TRACKING PRODUCTS IN A MEDICAL FACILITY

(71) Applicants: Richard Philippe, Laval (CA); Anders Larsson, Laval (CA)

(72) Inventors: Richard Philippe, Laval (CA); Anders Larsson, Laval (CA)

(73) Assignee: LOGI D INC., Laval (CA)

( * ) Notice: Subject to any disclaimer, the term of this patent is extended or adjusted under 35 U.S.C. 154(b) by 0 days.

(21) Appl. No.: 15/568,734

(22) PCT Filed: Apr. 21, 2016

(86) PCT No.: PCT/CA2016/050461
§ 371 (c)(1),
(2) Date: Oct. 23, 2017

(87) PCT Pub. No.: WO2016/168931
PCT Pub. Date: Oct. 27, 2016

(65) Prior Publication Data
US 2018/0090228 A1 Mar. 29, 2018

Related U.S. Application Data

(60) Provisional application No. 62/150,603, filed on Apr. 21, 2015.

(51) Int. Cl.
*G08C 19/00* (2006.01)
*G16H 40/40* (2018.01)
(Continued)

(52) U.S. Cl.
CPC ............. *G16H 40/40* (2018.01); *G06Q 10/08* (2013.01); *G06Q 10/087* (2013.01);
(Continued)

(58) Field of Classification Search
CPC .. G06K 19/0723; G06Q 10/08; G06Q 10/087; G06Q 50/22; G16H 10/60; G16H 40/40; G16H 40/63
(Continued)

(56) References Cited

U.S. PATENT DOCUMENTS 7,639,136 B1 * 12/2009 Wass ..................... G06Q 10/087
340/572.1
8,231,053 B2 7/2012 Linton et al.
(Continued)

FOREIGN PATENT DOCUMENTS

KR 10-1119511 2/2012
WO 2011/035277 3/2011
WO 2012/093801 7/2012

OTHER PUBLICATIONS

Philippe, Richard et al., Written Opinion of the International Searching Authority for PCT/CA2016/050461, dated Jul. 20, 2016.
(Continued)

*Primary Examiner* — Naomi J Small
(74) *Attorney, Agent, or Firm* — Woods Oviatt Gilman LLP; Dennis B. Danella, Esq.

(57) ABSTRACT

According to some aspects, a product tracking system, including a tracking module adapted to be affixed to a wall or other mounting location adjacent a receptacle for receiving products therein. The tracking module is operable to track products as they are discarded in the receptacle. The tracking module also includes at least one of a product detector, a patient detector, and an adding module.

14 Claims, 10 Drawing Sheets

(51) Int. Cl.
*G06Q 10/08* (2012.01)
*G16H 10/60* (2018.01)
*G16H 40/63* (2018.01)
G06Q 50/22 (2018.01)
G06K 19/07 (2006.01)

(52) U.S. Cl.
CPC ............ G16H 10/60 (2018.01); G16H 40/63 (2018.01); *G06K 19/0723* (2013.01); *G06Q 50/22* (2013.01)

(58) Field of Classification Search
USPC ........................................................ 340/5.92
See application file for complete search history.

(56) References Cited

U.S. PATENT DOCUMENTS

| | | | |
|---|---|---|---|
| 8,918,854 B1* | 12/2014 | Giobbi | H04W 4/80 726/9 |
| 2003/0182019 A1* | 9/2003 | Bonini | G16H 10/65 700/242 |
| 2006/0079994 A1* | 4/2006 | Chu | G06F 19/3462 700/231 |
| 2009/0138122 A1* | 5/2009 | Wagner | G07F 11/62 700/226 |
| 2009/0322486 A1 | 12/2009 | Gerstel | |
| 2010/0042437 A1* | 2/2010 | Levy | G16H 20/13 705/3 |
| 2010/0179822 A1* | 7/2010 | Reppas | G16H 40/20 705/2 |
| 2010/0332252 A1* | 12/2010 | Beraja | G06Q 40/00 705/2 |
| 2012/0173274 A1* | 7/2012 | Rensvold | G08B 21/245 705/2 |
| 2013/0325727 A1* | 12/2013 | MacDonell | A61B 50/13 705/308 |
| 2014/0316812 A1* | 10/2014 | Hathorn | G16H 10/60 705/3 |
| 2015/0161558 A1* | 6/2015 | Gitchell | G06K 7/10366 235/375 |
| 2015/0287305 A1* | 10/2015 | Iyer | G07C 9/27 340/572.1 |
| 2015/0332209 A1* | 11/2015 | DeBusk | G06Q 10/10 705/2 |
| 2016/0188840 A1* | 6/2016 | Eramian | G16H 20/13 700/237 |

OTHER PUBLICATIONS

Philippe, Richard et al., International Search Report for PCT/CA2016/050461, dated Jul. 20, 2016.

* cited by examiner

US 10,892,051 B2

SYSTEMS AND METHODS FOR AUTOMATICALLY TRACKING PRODUCTS IN A MEDICAL FACILITY

TECHNICAL FIELD

The embodiments herein relate to systems and methods for tracking products, and more particularly to systems and methods for automatically tracking products in facilities such as medical facilities.

INTRODUCTION

Today's health care facilities include a wide range of establishments, from small and relatively simple medical clinics to large and complex hospitals Health care facilities of all shapes and sizes use a large number of different products for treating patients having various health conditions.

In many cases, it is beneficial to keep track of products that have been used for treatment, or installed within patients, whether to ensure compatibility to contact patients for product recalls, or for billing, product replenishment, or other purposes. Keeping track of such products is a challenge, and is often performed manually. This may require users to manually enter data or take other actions, which is time consuming and can lead to user-generated errors.

Various solutions have been proposed for tracking products in a medical facility or the like. For instance, U.S. Pat. No. 7,839,136 to Wass et al. describes a system and method for tracking medical supplies using RFID tags.

U.S. Pat. No. 8,231,053 to Linton et al, describes a method and system for vending products from a defined area, such as a micro-warehouse with a door. The method includes fitting each product with a radio frequency identification (RFID) tag.

Other ways of monitoring product usage in health care facilities have beer disclosed. For example Canadian Patent Application No. 2,587,186 describes a system and method for automatically alerting hospital supply personnel when the amount of a given product falls below a threshold.

BRIEF DESCRIPTION OF THE DRAWINGS

For a better understanding of aspects of the system and method described herein, and to show more clearly how they may be carried into effect, reference will be made to the accompanying drawings in which.

DETAILED DESCRIPTION OF

Figure 1:
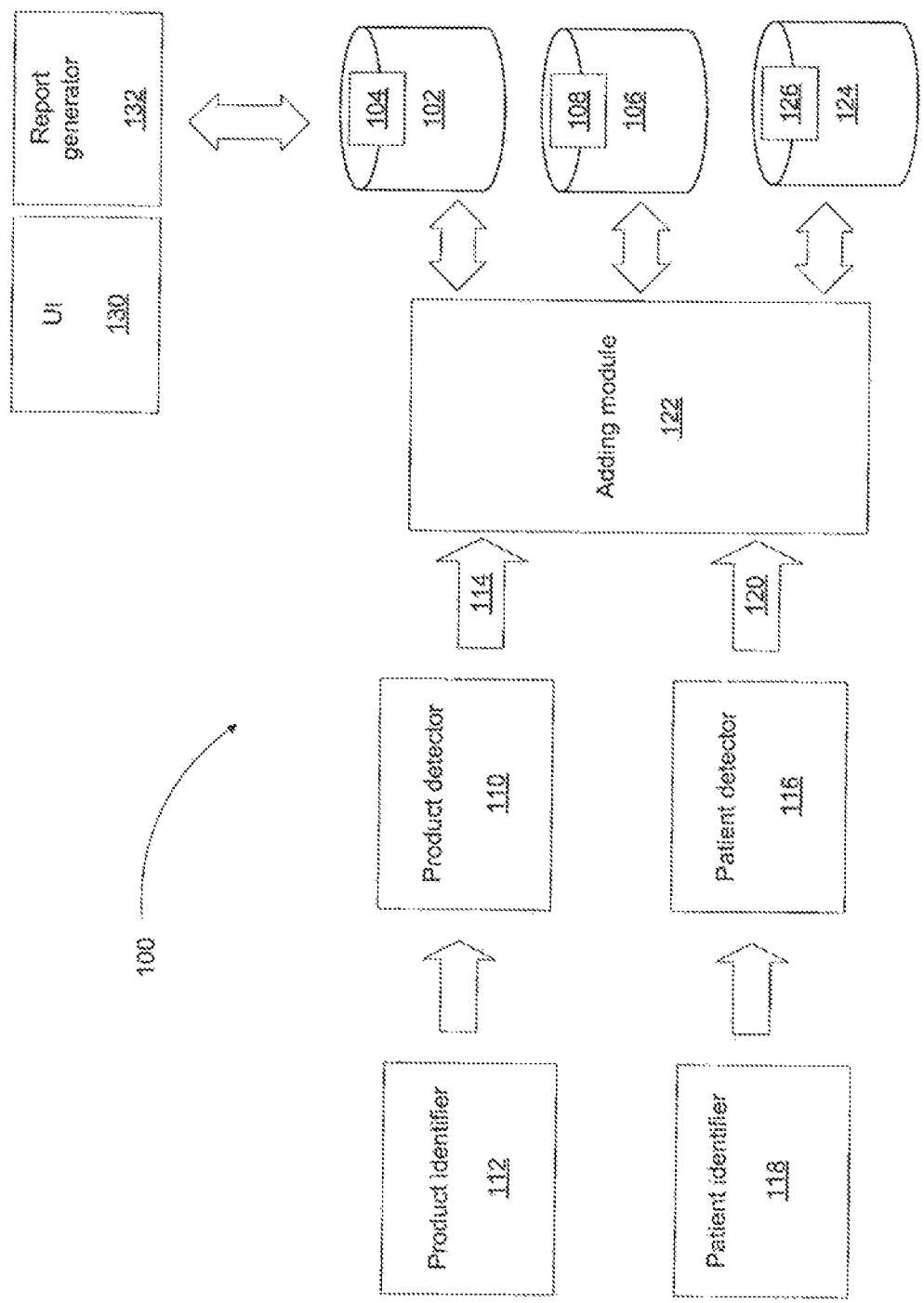
FIG. 1 is a block diagram of a system for adding a product information to a patient record according to one embodiment.

It will be appreciated that numerous specific details are set forth in order to provide a thorough understanding of the exemplary embodiments described herein. However it will be understood by those of ordinary skill in the art that the embodiments described herein may be practiced without these specific details. In other instances, well-known methods, procedures and components have not been described in detail so as not to obscure the embodiments described herein. Furthermore, this description is not to be considered as limiting the scope of the embodiments described herein in any way, but rather as merely describing the implementation of the various embodiments described herein.

The terms "an embodiment," "embodiment," "embodiments," "the embodiment," "the embodiments," "one or more embodiments," "some embodiments" and "one embodiment" mean "one or more (but not all) embodiments of the subject matter described in accordance with the teachings herein," unless expressly specified otherwise.

The terms "including" "comprising" and variations thereof mean "including but not limited to", unless expressly specified otherwise. A listing of items does not imply that any or all of the items are mutually exclusive, unless expressly specified otherwise in addition, the terms "a," "an" and "the" mean "one or more," unless expressly specified otherwise.

It will be appreciated that for simplicity and clarity of illustration where considered appropriate, reference numerals may be repeated among the figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein.

Some of the various embodiments of the systems and methods described herein may be implemented in hardware or software, or a combination of both. For example, some embodiments may be implemented in computer systems and computer programs, which may be stored on a physical computer readable medium (particularly a non-transitory computer readable medium), executable on programmable computers (e.g., computing devices and/or processing devices) that each comprise at least one processor, a data storage system (including volatile and non-volatile memory and/or storage elements), at least one input device (e.g., a keyboard, mouse or touchscreen), and at least one output device (e.g., a display screen, a network, or a remote server).

Further, although processes, methods, and the like may be described (in the disclosure and/or in the claims) having acts in a certain order, such processes and methods may be configured to work in alternate orders while still having utility. In other words, any sequence or order of actions that may be described does not necessarily indicate a requirement that the acts be performed in that order. The acts of processes and methods described herein may be performed in any order that is practical and has utility. Further, some actions may be performed simultaneously, if possible, while others may be optional, if possible.

When a single device or article is described herein, it may be possible that more than one device/article (whether or not they cooperate) may be used in place of a single device/article. Similarly, where more than one device or article is described herein (whether or not they cooperate), it may be possible that a single device/article may be used in place of the more than one device or article.

Some of the teachings herein relate to a system and method for adding product information to a patient record. More particularly, some embodiments relate to adding product information to a parent record for tracking purposes in a medical environment. Although the singular form may be used throughout the present specification and claims, it should be clear to those skilled in the art that in a medical environment, multiple products and patient records may be concurrently used and maintained, and that the present systems and methods may not be limited to the adding of one product information to one patient record, but rather may be applicable to the adding of product information to patient records in general.

Turning now to FIG. 1, illustrated therein is a system 100 for adding product information to a patient record. The system 100 includes a product database 102 for storing product information 104 for a product. To be specific, the product may correspond to one or many of a wide range of medical products such as medical implants, medical prostheses, medical substances or any other type of medical products used for treating, reconstructing or preventing a medical condition from occurring. The product information 104 may be stored in the product database 102 for example before the product is shelved for use; or when the product is received by a hospital.

The system 100 also includes a patient database 108 for storing a patient record 108, which could be a link to a hospital database. The patient record 108 generally corresponds to a description of an individual patient that is registered at a hospital. Usually, the patient record 108 holds entries that are given by the patient at patient registration.

In some cases, the product database 102 and the patient database 106 may be separate databases (as depicted on FIG. 1). In other examples they may be incorporated into one single database holding both the product information 104 the patient record 108.

As further shown in FIG. 1, the system 100 includes a product detector 110 for detecting a product identifier 112. In particular, the product identifier 112 corresponds to the product information 104 stored in the product database 102.

When the product identifier 112 is placed in proximity with the product detector 110, the product detector 110 detects the product identifier 112 and generates a corresponding product identifier message 114.

Generally, the product identifier 112 may be any type of electronically, optically or electromagnetically detectable identifier, such as for example a bar code label, a Radio Frequency identifier, a microchip, etc. In various embodiments, the product identifier 112 may be affixed to a product, or to a product container or on a product package, or pad of a label, and so on.

In this embodiment, the system 100 includes a patient detector 116 for detecting a patient identifier 118. More precisely, the patient identifier 118 generally corresponds to the patient record 108. The patient detector 116 detects the patient identifier 118 when the patient identifier is placed in proximity with the patient detector 116. Once the patient identifier 118 is detected, the patient detector 116 then generates a corresponding patient identifier message 120.

The patient identifier 118 may be any type of electronically or optically detectable identifier, such as for example a bar code label, a Radio Frequency identification (RFID) tag, a microchip, etc. The patient identifier 118 may be affixed to the patient affixed to a patient board, to a patient's bed, to a patient's bracelet, or to any other surface corresponding to or on the patient.

The system 100 of FIG. 1 may also include an adding module 122. The adding module 122 is adapted to receive (either directly or indirectly) the product identifier message 114 and the patient identifier message 120. Upon receipt of the product identifier message 114 and the patient identifier message 120, the adding module 122 acids the product information 104 to the patient record 108.

According to one aspect, the adding module 122 is wired or wirelessly connected to both the product detector 110 and the patient detector 118, and receives from them, respectively, the product identifier message 114 and the patient identifier message 120. Based on the received messages 114, 120, the adding module 122 adds the corresponding product information 104 to the corresponding patient record 108. In one aspect, the adding module 122 is adapted to store the product information 104 in the patient record 108. In another aspect, the adding module 122 is adapted to store the patient record 108 in the product information 104. In yet another aspect, the adding module 122 is adapted to store in a linking database 124 a link 128 that corresponds to the product information 104 and the patient record 108. In yet another aspect, instead of storing the product information 104 in the patient record 108 or vice versa, a software pointer may be used to link directly the product information 104 and the patient record 108.

According to one aspect of the system 100, the databases (102, 106 and 124) are located in a central server that is adapted to connect to a local network of the hospital or other medical facility. When the adding module 122 is also connected to the local network. It is possible for the adding module 122 to access the databases (102, 106 and 124) by connecting to the central server. Consequently, it is possible for multiple adding modules 122 to access the same databases (102, 106 and 124) simultaneously, when multiple patients receive medical care at the same time. Moreover, there is no need for the adding module 122 to make a database selection according to the product information 104 or to the patient record 108. Since all databases (102, 106 and 124) are centralized, each product information 104 may be stored in the same product database 102 and each patient record 108 is stored in the same patient database 106.

It will be understood by a skilled reader that it is possible for the linking database 124 end the patient database 106 to be implemented as one single database and that it is also possible for the linking database 124 and the product database 102 to be implemented as one single database.

Figure 2:
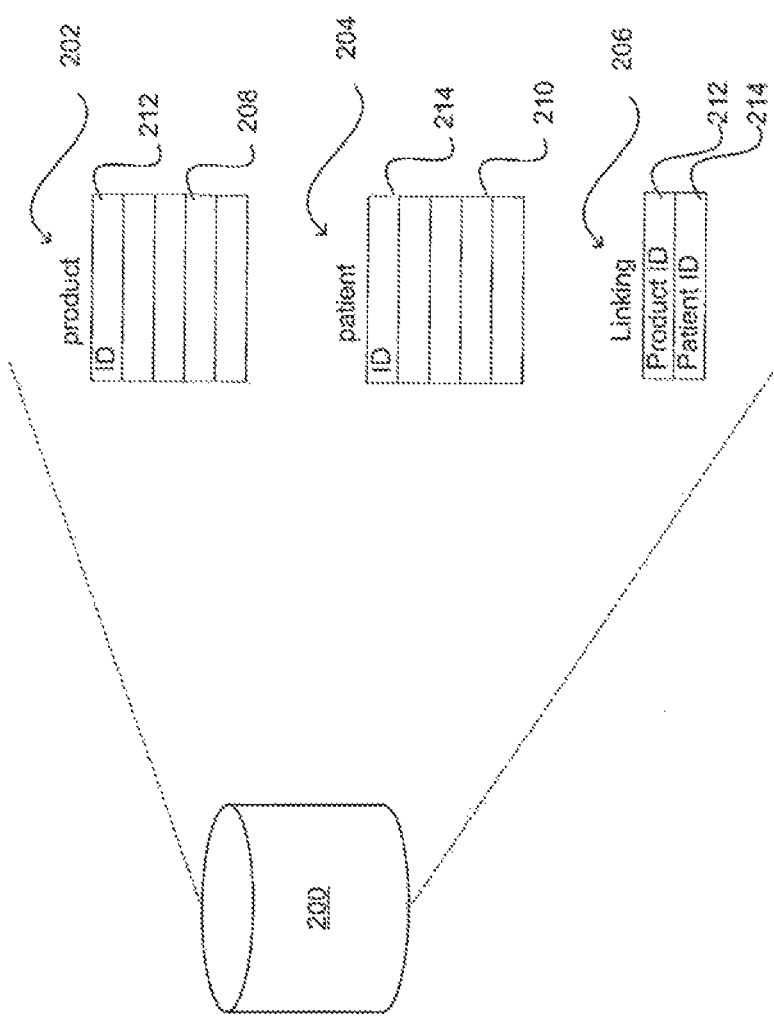
FIG. 2 is an exemplary database diagram according to one embodiment.

Turning now to FIG. 2, according to another embodiment, the product database 102, the patient database 106 and the linking database 124 may be the same database 200. The database 200 comprises a product table 202, a patient table 204 and a linking table 206. In both the product fable 202 and the patient table 204 there are various attribute fields, such as a product attribute field 203 and a patient attribute field 210, for respectively defining the product information 104 and the patient record 108.

Moreover, in both the product table 202 and the patient table 204 there are a reference field, such as a product reference field 212 and a patient reference field 214, for respectively referencing the product information 104 and the patient record 108.

Although the number and the type of attribute fields 208 is variable, in one exemplary aspect, the product information 104 can include one or more of the following attribute fields 208: product code, product serial number, product lot number, product name, product purchase date, product expiry date, product supplier contact information, product manufacturer's number and other information pertinent to the product.

On the other hand, the patient record 108 may include least one of the following attribute fields 210: a patient number, an event number, patient hospital card number, patient medical insurance number, patient name, patient date of birth, patient gender patient contact information, patient emergency contact information. Alternately, the product information 104 and the patient record 108 could include one or several of the listed attribute fields.

Further shown in FIG. 2 is the linking table 206 that comprises the product reference field 212 and the patient reference field 214. These reference fields together form the link 126 which corresponds to adding the referenced product information 104 to the referenced patient record 108. Thus, in the event of a product recall, where a particular product having a given serial number or lot number needs to be retraced, it may be possible with the present system 100, to find the patient(s) on whom the particular product was used or implanted.

Returning again to FIG. 1, according to some aspects, the system 100 may further include a user interface module 130 for allowing a user to retrieve data stored in at least one of the databases (102, 106 and 124). It is possible for the user to retrieve various types of data corresponding to either the product information 104, the patient record 108 or the link 126. According to one aspect, the user interface module 130 allows a user to retrieve "patient contact information" based on a "product serial number". With this user interface module 130, it is possible for the user to trace the patient(s) on which a specific product has been used.

According to another case, the user interface module 130 allows the user to retrieve a "product serial number" based on a "patient hospital card number". Furthermore, it is possible for the user to list the products that have been used in or on a specific patient. Depending on the various attribute fields that define either the product information 104 or the patient record 108, the user interface module 130 allows the user to perform correlations and extract corresponding resulting data.

Moreover according to yet another aspect, the system 100 may further include a reporting module 132. The reporting module 132 is adapted to produce a report according to data corresponding to either: the product information 104, the patient record 108 or the link 126. The reporting module 132 is adapted to produce a report based on a request of the user through the user interface module 130.

In one aspect the reporting module 132 is adapted to produce a report for tracking purposes. In another aspect the report module 132 is adapted to produce a report for managing the product expiry date or a product close to the expiry date. When one or more products reach the set criteria, the report module 132 is adapted to automatically send the report to a user or a supplier to have the product replaced.

Figure 3:
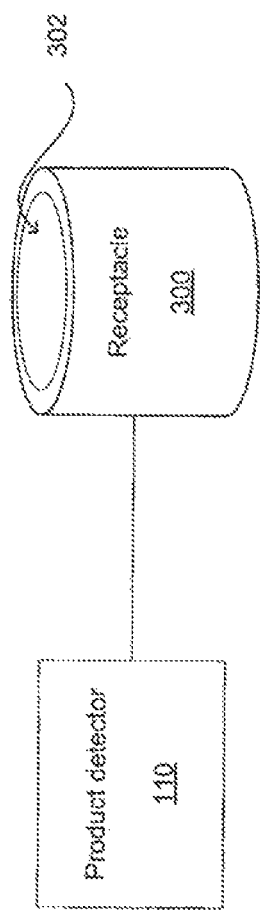
FIG. 3 is a block diagram of a product detector affixed to a receptacle according to one embodiment.

Turning now to FIG. 3, in some embodiments the product detector 110 is affixed to a receptacle 300. In one example, the receptacle 300 is a bin (also called a "waste basket" or "garbage receptacle") for receiving products and/or packages to be discarded.

For instance, once the product package is opened, and the product contained therein is withdrawn from the product package for use on a patient, the product package may be discarded into the receptacle 300.

According to one aspect, the product detector 110 is adapted to detect the product identifier 112 when the product package enters the receptacle 300. In this aspect, the product detector 110 is directed towards an opening 302 of the receptacle 300 and, as the product package passes through the opening 302, the product detector 110 will detect the product identifier 112 that is affixed to the product package.

According to another aspect, the product detector 110 is adapted to detect the product identifier 112 once the product package is already received Within the receptacle 300. In this aspect, the product detector 110 may be directed towards an inner side of the receptacle 300 and once the product package is in the receptacle 300, the product detector 110 will detect the product identifier 112 that is affixed to the product package.

According to yet another aspect, the product detector 110 is adapted to generate the product identifier message 114 only once, after the product package is placed in the receptacle 300. In this aspect, the product detector 110 comprises a memory for storing a list of detected product identifiers. As the product identifier 112 is detected, the product detector 110 compares the product identifier 112 to the list, and if there is a match, the product detector 110 does not generate the product identifier message 114.

However, if there is no match, the product detector 110 generates the product identification message 114 and then adds the product identifier 112 to the list. This reduces the number of product, identification messages 114 that are generated and liberates the adding module 122 from having to verify whether there is duplication in the received product identifier messages 114.

Figure 4:
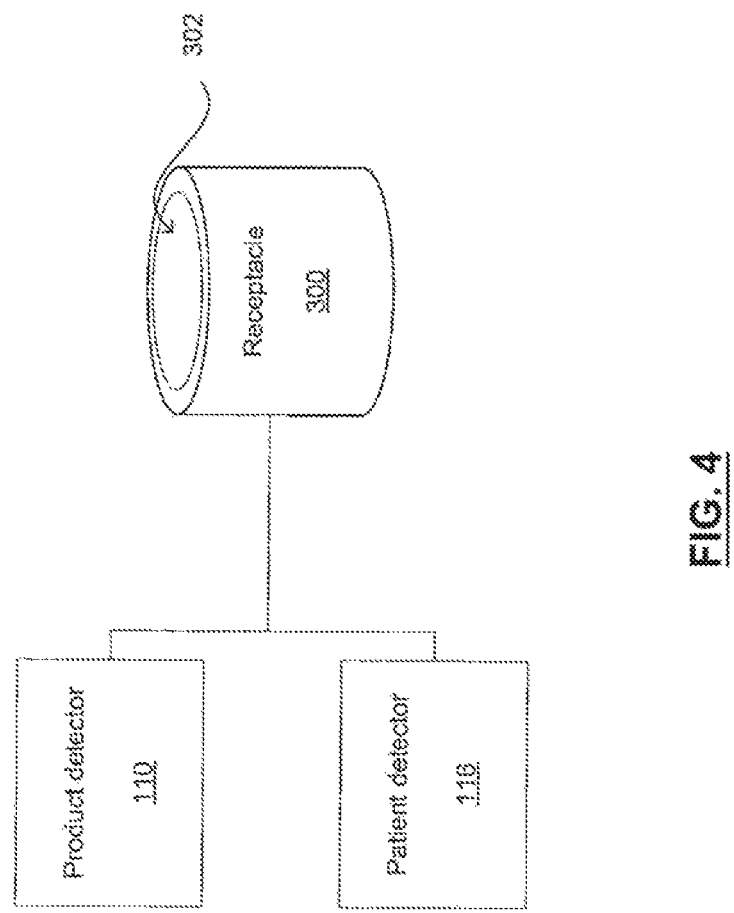
FIG. 4 is a block diagram of the product, detector and a patient detector that are affixed to the receptacle according to one embodiment.

Turning now to FIG. 4, in this embodiment both the product detector 110 and the patient detector 116 are affixed to the receptacle 300.

In some embodiments, the receptacle 300 may be mobile. For example, the receptacle 300 may be provided with wheels and be moved around as desired, such as in proximity to where medical care is being given.

In some cases, the patient defector 116 is adapted to detect the patient identifier 118 when the patient or the patient identifier 118 comes in proximity with the receptacle 300, such as for example when the patient enters a room where the receptacle 300 is located. The room may be any type of area that is enclosed, semi-enclosed or open. In one aspect, the room is a hospital room where medical care is normally given to the patient. In another aspect, the location is a mobile hospital bed where the patient is normally laid down for receiving medical care, etc. As the patient or the patient identifier 118 comes in proximity with the patient detector 118, the patient identifier 118 is detected.

Thereafter, when medical care is given to the patient and products are used on that patient, for each product used the product identifier 112 can be detected once the product package (or the consumed product itself) is thrown into the receptacle 300. The corresponding product information 104 is then added to the patient record 100 corresponding to the last detected patient identifier 118.

According to another aspect, the patient detector 116 is adapted to detect the patient identifier 118 when the patient, identifier 118 has been in proximity therewith for a certain time. In this aspect, the patient detector 116 may be directed toward a specific location where the patient is usually placed for receiving care.

Furthermore, the patient detector 116 may be adapted to generate the patient identifier message 120 only once, thus reducing the number of patient identification messages 120 generated and liberating the adding module 122 from having to make a verification of whether there is duplication in the received patient identifier messages 120.

In some embodiments, the patient detector 116 may also be a card that is brought in proximity or that is inserted into the receptacle 300. A keypad or other input device (i.e., a touchscreen) may also be used to enter the patient identifier 118 into the receptacle 300.

Figure 5:
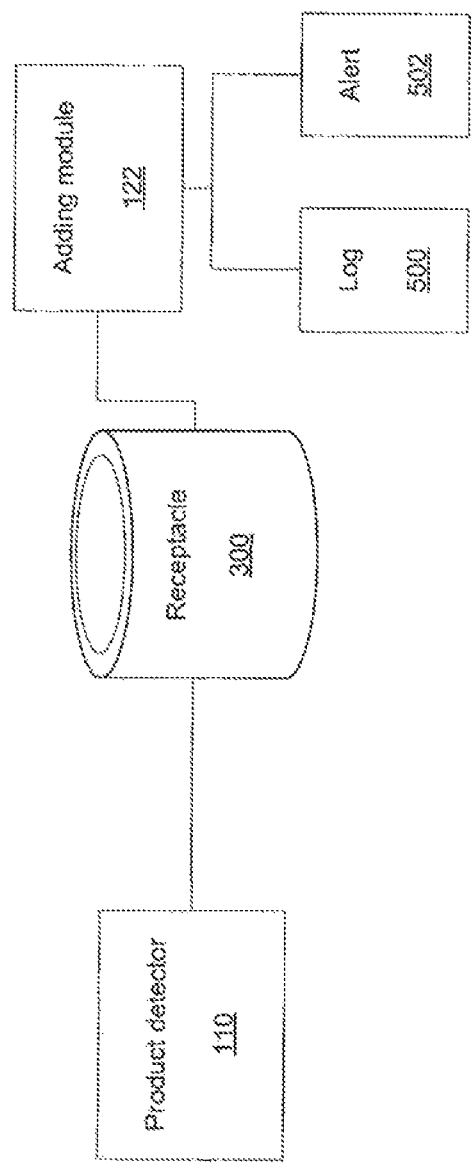
FIG. 5 is a block diagram of the product detector and an adding module affixed to the receptacle according to one embodiment.

Turning now to FIG. 5, according to another embodiment of the system 100, the product detector 110 may be affixed to the receptacle 300 along with the adding module 122. This embodiment may enable the addition of the product information 104 to the patient record 108 from the receptacle 300. Consequently, risk of losing a product identifier message 114 may be reduced or lowered. Moreover the product identifier message 114 may be more quickly received by the adding module 122 since there is no need for the message 114 to travel through a communication network to reach the adding module 122. This may facilitate instantaneous (or near-instantaneous) tracking of products that have been used on the patient.

According to another aspect, a logging module 500 may be connected to the adding module 122. Once the product information 104 is added to the patient record 108, the adding module 122 generates a description of the addition process. To do so, the adding module 122 queries the database that holds the product attribute fields 208 and the patient attribute fields 210, and the adding module 122 then generates the description of the addition process.

The logging module 500 then uses the description of the addition process and produces a log. The description or the addition process may comprise one or more attributes, such as: a patient hospital card number, a patient name, a product serial number, a product name, a product expiry date and a time and date at which the addition process took place.

According to yet another embodiment, an alert module 502 may be connected to the adding module 122. Before adding the product information 104 to the patient record 108, the adding module 122 verifies if there are any existing errors that may render the addition process impossible or undesirable. When an error or a counter-indication exists, the adding module 122 may generate an error message and the alert module 502 can generate an alert to inform the medical personal of the error or counter indication. Various causes of error may be possible, such as reaching a product's expiry date.

Figure 6:
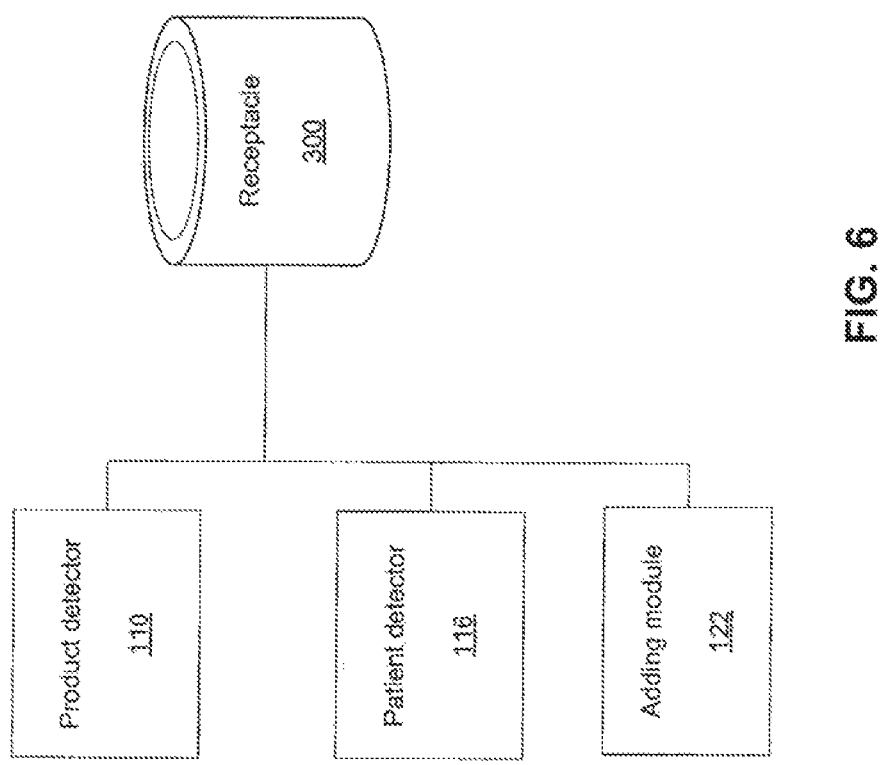
FIG. 6 is a block diagram of the product detector the patient detector and the adding module affixed to the receptacle according to one embodiment.

Turning now to FIG. 6, according to some embodiments of the system 100, the product detector 110, the patient detector 116 and the adding module 122 are all affixed to the receptacle 300, and are in direct connection therebetween. In this particular aspect, the addition process of the product information 104 to the patient record 108 takes place at the receptacle 300. As both the product detector 110 and the patient detector 116 are affixed to the receptacle 300, the risk of losing either of the product identifier message 114 or the patient identifier message 120 before the adding module 122 receives the messages 114, 120 may be lower.

A skilled reader will recognize that it is possible for the databases (102, 106, 124, 200), the product defector 110, the patient detector 116 or the adding module 122 to either be independently connected, connected to one another or to be connected to any other part of the system 100 without, affecting the workings of the system 100. The connection therebetween may be done through a wired or a wireless network, and may generally be direct or indirect.

The product detector 110 and the patient detector 116 thus receive the product identifier message 114 and the patient identifier message 120 (respectively), and send the product identifier message 114 and the patient identifier message 120 to the adding module 122, which may be co-located, or separated therefrom. Generally any type of communication means and standards may be used to send the patient identifier message 120 and product identifier message 114 to the adding module 122.

Figure 7:
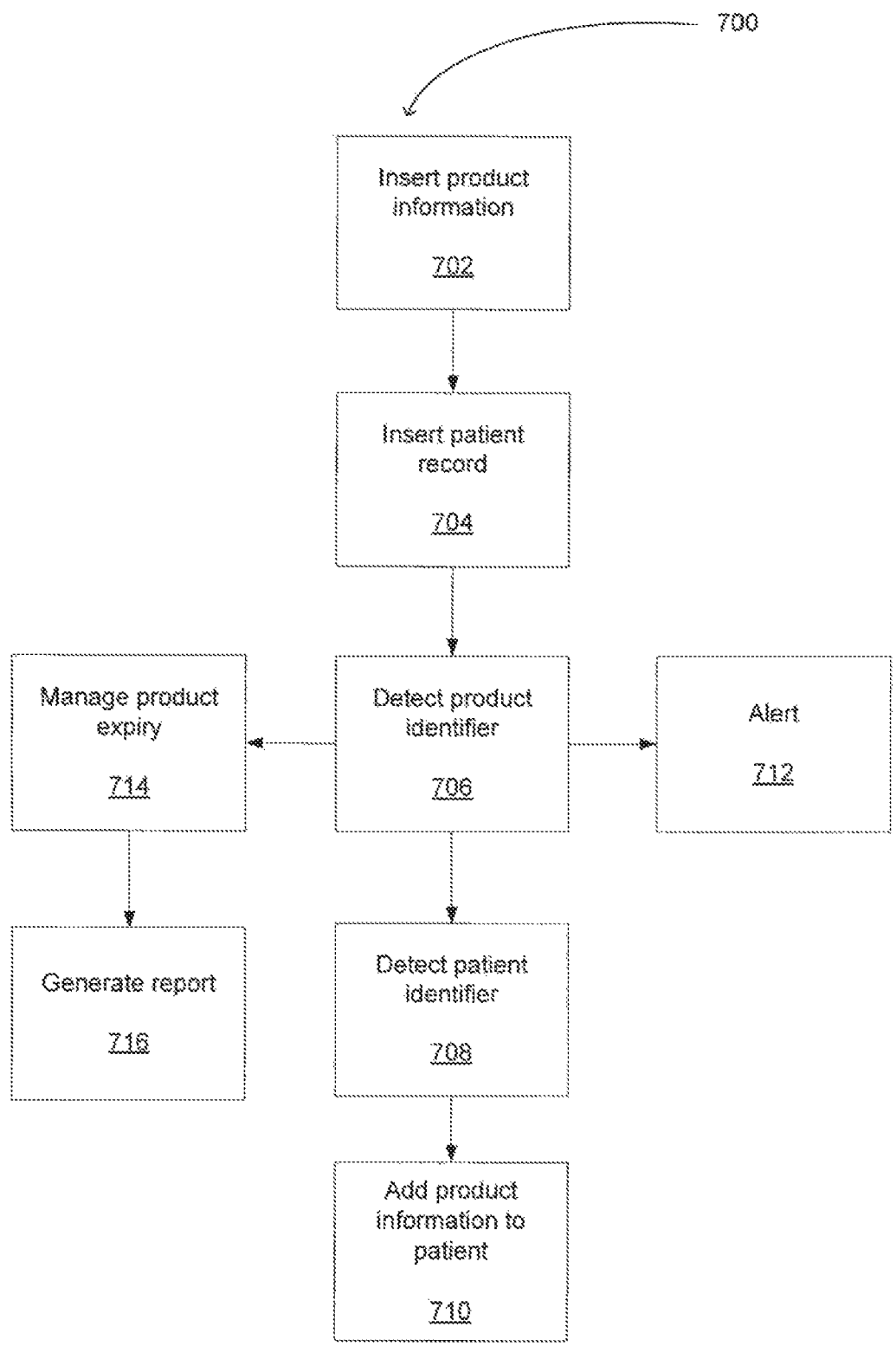
FIG. 7 is a flow diagram of a method for adding product information to a patient record according to one embodiment.

Turning now to FIG. 7, illustrated, therein is a method 700 for adding product information to a patient record. The method 700 includes inserting product information 702 into a product database (i.e., the product information 104 into the product database 102), and inserting a patient record 704 into a patient database (i.e., the patient record 108 into the patient database 106).

Moreover, the method 700 also includes detecting the product identifier 706 corresponding to the product information, and detecting the patient identifier 708 corresponding to the patient record.

The method 700 also includes adding the product information to the patient record 710.

In some embodiments, the method 700 further includes alerting 712 a user when an incompatibility is detected with the product information 104. According to another aspect, the method 700 further comprises managing 714 a product expiry date for identifying an expired product and generating 716 a report for notifying the user or the supplier (or both) that the identified expired product must be replaced.

Figure 8:
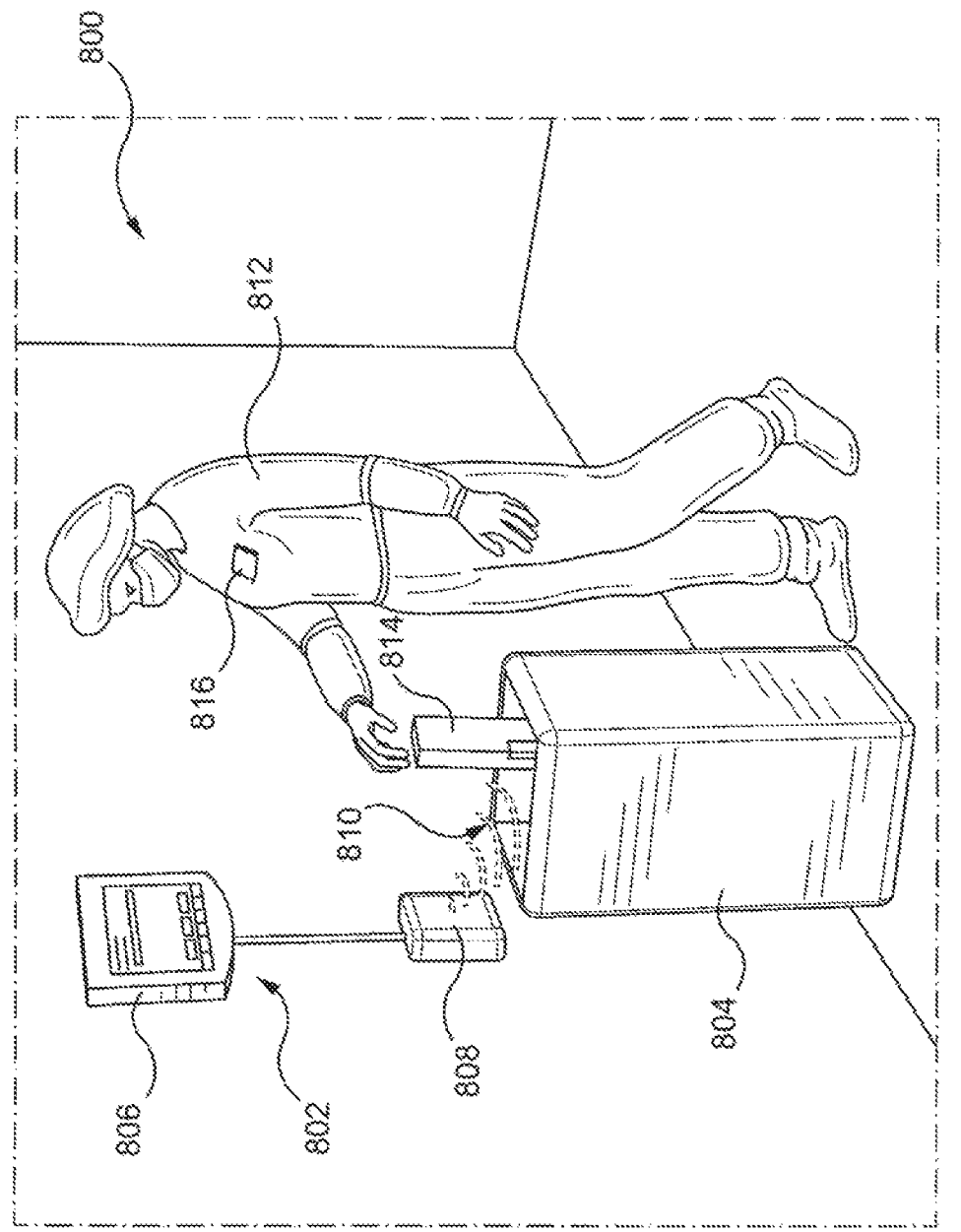
FIG. 8 is an illustration of a product tracking system according to another embodiment.

Turning now to FIG. 8, illustrated therein is a product tracking system 800 according to another embodiment.

In this embodiment, the system 800 comprises a tracking module 802 that is adapted to be affixed to a wall or other mounting location (such as on a vertical sidewall of a cabinet), and which is adjacent or near a receptacle 804 (i.e., a "waste basket" or "garbage receptacle") for receiving products and/or packages to be discarded. The tracking module 802 is operable to track products and/or packages as they are discarded.

In particular, in this embodiment, at least one of the product detector 110, the patient detector 118, and the adding module 122 are provided in the tracking module. For instance, once the package 814 of a product is opened, and the package 814 is discarded into the receptacle 804 (i.e. via the opening 810 of the receptacle), an antenna module 808 of the tracking module 802 (which may include the product defector 110) can detect the product identifier 112 on the packaging 814 and provide a suitable action, such as updating a patient record.

In some embodiments, the tracking module 802 may also include a I/O device 804 which could include for example a touchscreen kiosk. The I/O device 804 can allow a user 812 (such as a medical practitioner) to configure the tracking module 802, such as by displaying and manipulating a particular patient record, identifying a room location, and so on.

In some embodiments, the I/O device 804 and/or the antenna 808 may communicate with an ID badge 816 or other identification module worn or carried by the user 812, such as using an RFID tag or the like in some embodiments, identification module could be a smart phone or other device, and which may be configured using an application.

This may allow the tracking module 802 to confirm that an authorized user is disposing of articles in the receptacle 804.

Generally speaking, the receptacle 804 may be any suitable receptacle, and in particular may be an existing waste receptacle that is used by a medical facility, in this manner the system 800 can be used to "retrofit" facilities that already have existing waste bins. This can be helpful to save costs, since custom waste bins need not be purchased, and if may also be helpful to save space. In particular, since the tracking module 802 can be mounted on a wall above or adjacent an existing waste bin, additional floor space in a medical facility need not be occupied.

Figure 9:
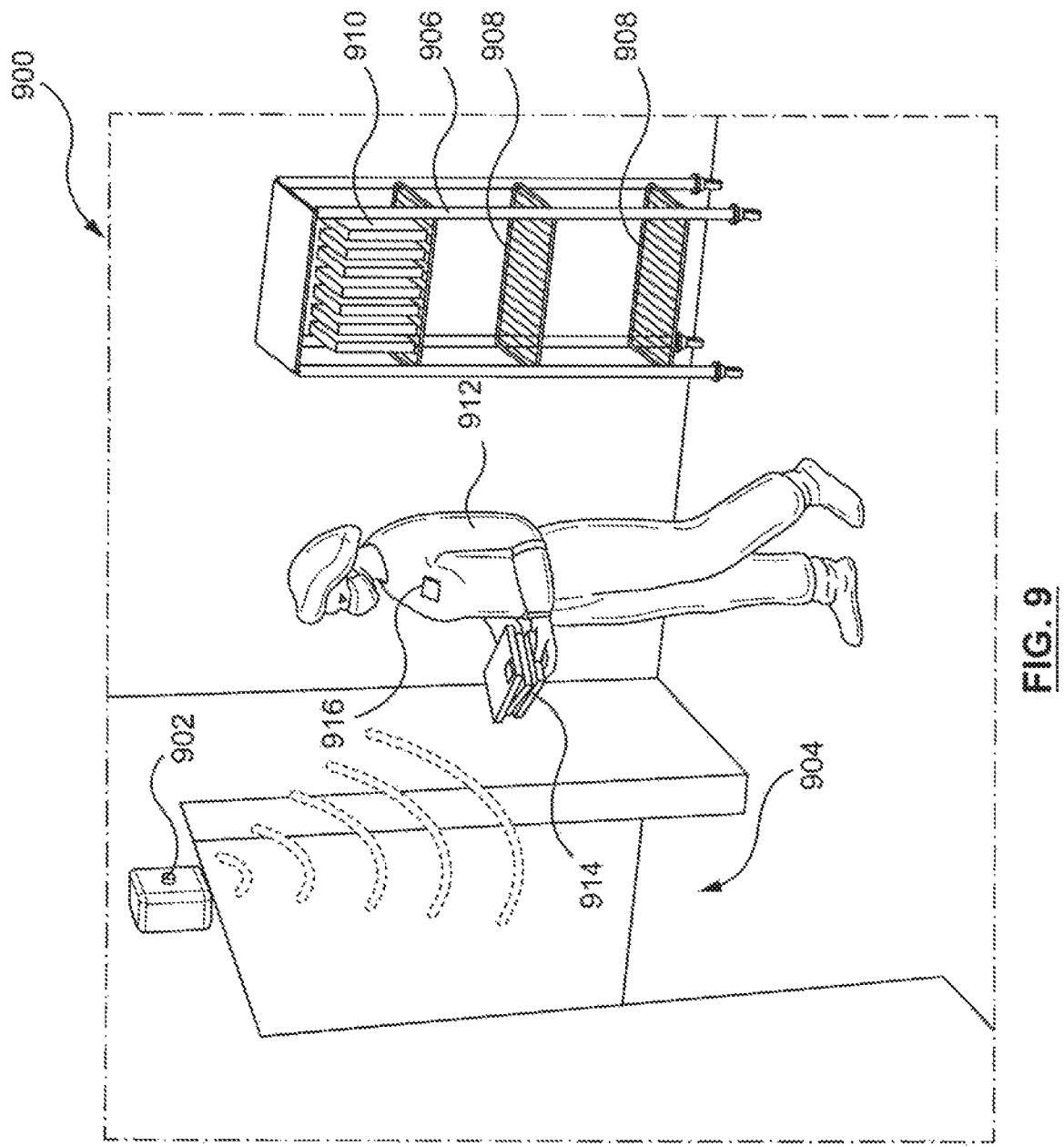
FIG. 9 is an illustration of a product tracking system according to yet another embodiment.

Turning now to FIG. 9, illustrated therein is a product tracking system 900 according to yet another embodiment. In this embodiment a tracking module 902 is mounted above an opening, such as a doorway 904 or other opening in a room or hallway. This tracking module 902 can be used to track the movement of products to and from the particular room by monitoring products as the pass through the doorway 904. For instance, this room may contain a rack 906 with several shelves 908 that store medical products 910 thereon. When a user 912 moves one of the products (such as product 914) through the doorway, the tracking module 902 can observer a product identifier 112 thereon, and update a suitable record.

For example, the doorway 904 may be the doorway to an operating room; as the medical product 814 (i.e., an implant) is carried into the operating room the tracking module 902 can record information about the medical product 814 and update a patient record, or create a record, or take other action(s).

In some cases this information can be reconciled with information collected when the packaging of the product is discarded, for instance to confirm that the particular medical product 914 was actually consumed during a medical procedure, and was not returned into inventory.

In some embodiments, the tracking module 302 may communicate with an ID badge 916 or other identification module affixed to or earned by the user 912. This may allow the tracking module 902 to confirm who was moving the product 914 through the doorway 304; which may be helpful for authentication purposes for example.

Tracking products using the tracking system 900 can be more cost effective than other inventory management systems. For instance, it may be possible to have a tracking system with one or more individual tracking units associated with the rack 906, and/or the shelves 908 and/or the medical products 910 (i.e. RFID cabinets) However, having a number of tracking units can be cumbersome and expensive, and may require customized racks or shelving, or at least retrofitting existing units.

In contrast, by providing a tracking module 902 at a point of entrance or egress for products (i.e., on the lintel above a doorway), a smaller number of tracking modules 902 may be used to track the in and out movement of medical products within a medical facility.

Figure 10:
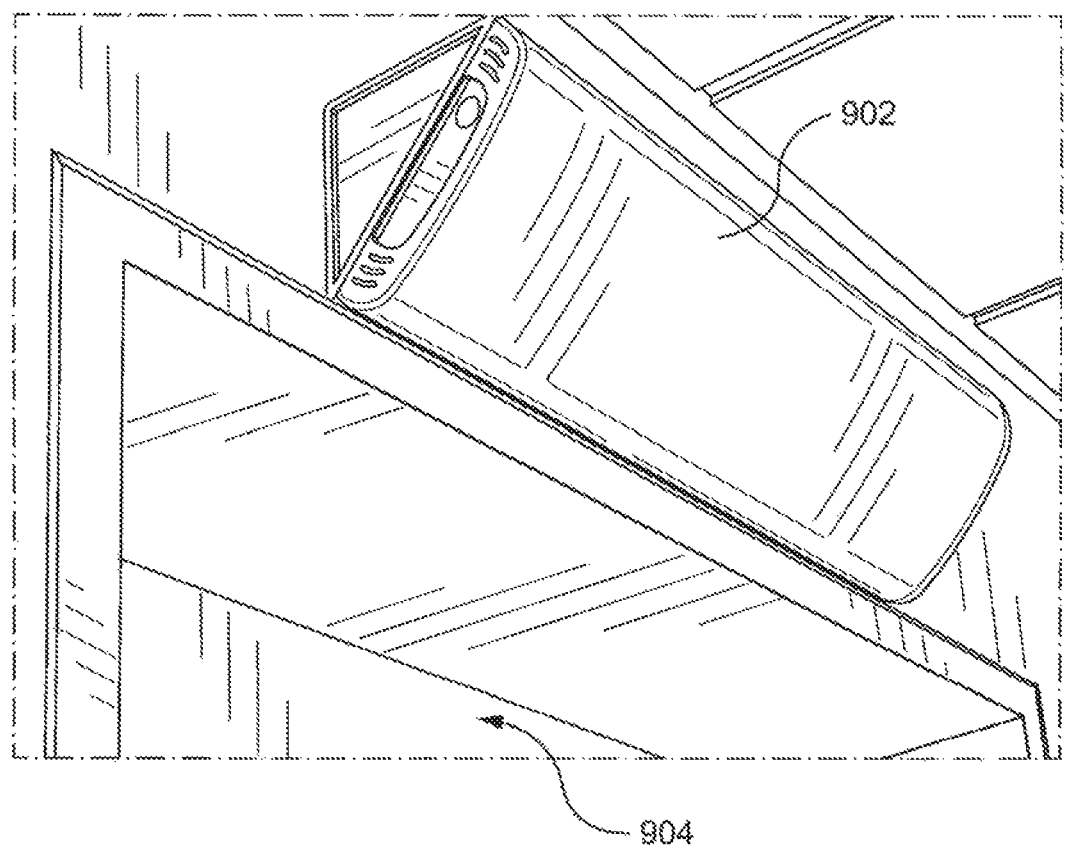
FIG. 10 is an exemplary image of a product tracking system according to another embodiment.

Turning now to FIG. 10, this image shows another example product tracking module 802 mounted over a doorway 904 according to another embodiment.

Although various exemplary embodiments have been described herein. It will be appreciated that other specific embodiments will be possible based on the teachings herein and without departing from the spirit and scope of the claimed embodiments.

The invention claimed is:

1. A product tracking system, comprising:
a tracking module adapted to be affixed to a wall or other mounting location adjacent a receptacle for receiving a product therein, the tracking module operable to track the product as it is discarded in the receptacle by a user;
the tracking module comprising a product detector and a patient detector,
the patient detector adapted to detect a patient identifier when the patient identifier has been in proximity therewith for a predetermined time,
wherein the tracking module is operable to communicate with an identification module worn or carried by the user to confirm that the user is an authorized user discarding the product in the receptacle.

2. The product tracking system of claim 1, further comprising an antenna module adapted to detect a product identifier on a packaging discarded in the receptacle.

3. The product tracking system of claim 2, wherein the tracking module is operable to update a patient record when the antenna module detects the packaging discarded in the receptacle.

4. The product tracking system of any one of claims 1-3, further comprising an I/O device operable to allow a user to configure the tracking module.

5. The product tracking system of claim 4, wherein the I/O device comprises a touchscreen kiosk.

6. The product tracking system of claim 4, wherein the user can configure the tracking module by displaying and manipulating a particular patient record.

7. The product tracking system of claim 4, wherein the user can configure the tracking module by identifying a room location.

8. The product tracking system of claim 4 wherein at least one of the I/O device and the antenna module are in communication with the identification module.

9. The product tracking system of claim 8 wherein the identification module is an ID badge worn or carried by the user.

10. The product tracking system of claim 8, wherein the identification module includes an RFID tag.

11. The product tracking system of claim 8 wherein the identification module includes a smartphone.

12. The product tracking system of claim 11, wherein the smartphone may be configured using an application.

13. The product tracking system of claim 8 wherein the tracking module is operable to communicate with the identification module worn on an upper body of the user to confirm that the user is the authorized user.

14. The product tracking system of claim 5, wherein the tracking module is mounted to the wall or other mounting location adjacent a top of the receptacle, and the touchscreen kiosk is mounted to the wall or other mounting location above the tracking module spaced from the tracking module and the top of the receptacle.

* * * * *